US00PP36542P2

(12) United States Plant Patent
van Swieten

(10) Patent No.: US PP36,542 P2
(45) Date of Patent: Mar. 11, 2025

(54) ***PHALAENOPSIS* PLANT NAMED 'PHA568949'**

(50) Latin Name: *Phalaenopsis hybrida*
Varietal Denomination: PHA568949

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/769,864

(22) Filed: Jul. 11, 2024

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Phalaenopsis* plant named 'PHA568949', characterized by its compact and upright plant habit; moderately vigorous to vigorous growth habit and moderate growth rate; strong flowering stems; strong leaves; freely flowering habit with typically five inflorescences developing per plant, each inflorescence with numerous flowers; white-colored flowers with greenish yellow-colored labellum; and good postproduction longevity.

2 Drawing Sheets

Figure 1:
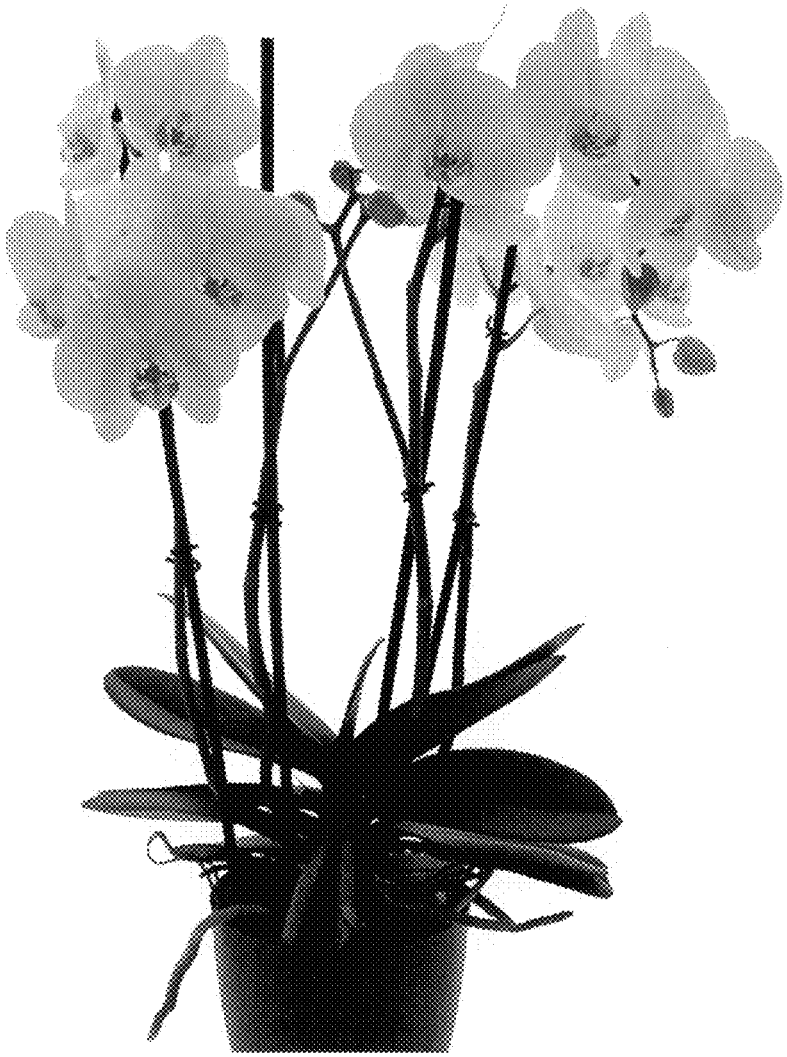

Botanical designation: *Phalaenopsis hybrida.*
Cultivar denomination: 'PHA568949'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B. V. of Bleiswijk, The Netherlands on Apr. 19, 2023, application number 2023/0876. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'PHA568949'.

The new *Phalaenopsis* plant is a product of a planned breeding program conducted by the Inventor in Bleiswijk, The Netherlands. The objective of the breeding program is to develop new compact and freely flowering *Phalaenopsis* plants with flowers with unique patterns and coloration.

The new *Phalaenopsis* plant originated from a cross-pollination in December 2015 in Bleiswijk, The Netherlands of a proprietary selection of *Phalaenopsis hybrida* identified as code number 07-1-9058, not patented, as the female, or seed, parent with a proprietary selection of *Phalaenopsis hybrida* identified as code number 09-43398-01, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in September 2018.

Asexual reproduction of the new *Phalaenopsis* plant by in vitro meristem propagation in a controlled environment in Bleiswijk, The Netherlands since September 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA568949'. These characteristics in combination distinguish 'PHA568949' as a new and distinct *Phalaenopsis* plant:

1. Compact and upright plant habit.
2. Moderately vigorous to vigorous growth habit and moderate growth rate.
3. Strong flowering stems.
4. Strong leaves.
5. Freely flowering habit with typically five inflorescences developing per plant, each inflorescence with numerous flowers.

6. White-colored flowers with greenish yellow-colored labellum.
7. Good post production longevity.

Plants of the new *Phalaenopsis* can be compared to plants of the female parent selection. Plants of the new *Phalaenopsis* differ primarily from plants of the female parent selection in flower size as flowers of plants of the new *Phalaenopsis* are broader than flowers of plants of the female parent selection.

Plants of the new *Phalaenopsis* can be compared to plants of the male parent selection. Plants of the new *Phalaenopsis* differ primarily from plants of the male parent selection in leaf orientation as leaves of plants of the new *Phalaenopsis* are horizontal to semi-erect whereas leaves of plants of the male parent selection are semi-erect. In addition, the lateral lobes of the labella of plants of the new *Phalaenopsis* are more curved than the lateral lobes of the labella of plants of the male parent selection.

Plants of the new *Phalaenopsis* can be compared to plants of *Phalaenopsis hybrida* 'PHA1794396', not patented. In side-by-side comparisons, plants of the new *Phalaenopsis* differ primarily from plants of 'PHA1794396' in the following characteristics:

1. Leaves of plants of the new *Phalaenopsis* are horizontal to semi-erect whereas leaves of plants of 'PHA1794396' are semi-erect.
2. Leaves of plants of the new *Phalaenopsis* are shorter than leaves of plants of 'PHA1794396'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA568949' grown in a container.

Figure 2:
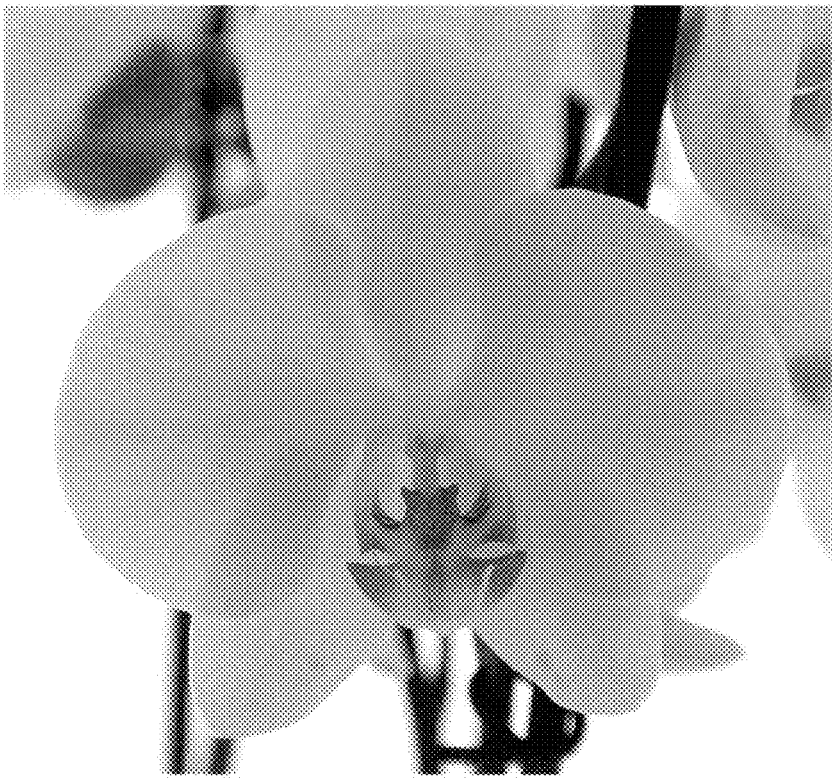

The photograph on the second sheet (FIG. 2) is a close-up view of a typical flower of 'PHA568949'.

DETAILED BOTANICAL DESCRIPTION

The aforementioned photographs and following observations and measurements describe plants grown during the late winter and early spring in 12-cm containers in a glass-covered greenhouse in Bleiswijk, The Netherlands and under cultural practices typically used in commercial *Phalaenopsis* production. Plants were 18 months old when the photographs and description were taken. During the first 14 months of production of the plants, day and night temperatures averaged 28.5° C.; and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA568949'.

Parentage:

*Female, or seed, parent*.—Proprietary selection of *Phalaenopsis hybrida* identified as code number 07-1-9058, not patented.

*Male, or pollen, parent*.—Proprietary selection of *Phalaenopsis hybrida* identified as code number 09-43398-01, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; sparse.

Plant description:

*Plant form and growth habit*.—Herbaceous epiphyte; compact and upright plant habit with typically five inflorescences developing per plant, each inflorescence with numerous flowers; monopodial; moderately vigorous to vigorous growth habit and moderate growth rate.

*Plant height, substrate level to top of foliar plane*.—About 16.9 cm.

*Plant height, substrate level to top of floral plane*.—About 38.3 cm.

*Plant diameter or spread*.—About 33.8 cm.

Leaf description:

*Arrangement and quantity*.—Distichous, simple; sessile; about six to nine fully-developed leaves per plant.

*Length*.—About 13.7 cm.

*Width*.—About 7 cm.

*Aspect*.—Horizontal to semi-erect.

*Shape*.—Obovate; slightly carinate.

*Apex*.—Unequal obtuse.

*Base*.—Sheathing. Sheath length: About 1.6 cm. Sheath width: About 1.5 cm. Sheath color: Close to 143C.

*Margin*.—Entire; not undulate.

*Texture and luster, upper surface*.—Smooth, glabrous; slightly glossy.

*Texture and luster, lower surface*.—Smooth, glabrous; matte.

*Venation pattern*.—Camptodromous.

*Color*.—Developing leaves, upper surface: Close to NN137A. Developing leaves, lower surface: Close to a blend of 146A and 146B with narrow marginal edges, close to 144B. Fully expanded leaves, upper surface: Close to NN137A with margins, close to 144A; venation, close to a blend of NN137A and 139A. Fully expanded leaves, lower surface: Close to 146B with margins, close to 147B; venation, close to 147A.

Inflorescence description:

*Appearance and flowering habit*.—Showy zygomorphic flowers arranged on axillary simple or branched racemes; typically five inflorescences develop per plant; each inflorescence with about ten flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about nine weeks on the plant; flowers not persistent.

*Inflorescence length* (*lowermost flower to inflorescence apex*).—About 19.5 cm.

*Inflorescence width*.—About 13.4 cm.

*Flower buds*.—Height: About 1.8 cm. Diameter: About 1.2 cm by 1.4 cm. Shape: Broadly ovate. Color: Close to 145A, 145B and 144C.

*Flower size*.—About 6.8 cm (vertical) by 7.3 cm (horizontal).

*Flower depth*.—About 2.6 cm.

*Petals, quantity and arrangement*.—Three, two lateral petals and one center petal transformed into a labellum.

*Lateral petals*.—Length: About 3.6 cm. Width: About 4.3 cm. Shape: Broadly deltoid-reniform to broadly lunate. Apex: Obtuse to shallow and broadly retuse. Margin: Entire; not undulate. Texture and luster, upper and lower surfaces: Smooth, glabrous, moderately velvety; matte. Color: When opening, upper surface: Close to 155C. When opening, lower surface: Close to 155C; towards the center and base, close to a blend of 145D and 157B. Fully opened, upper and lower surfaces: Close to NN155D; color does not change with subsequent development.

*Labella*.—Appearance: Three-parted with two lateral lobes and a central lobe. Length, lateral lobes: About 1.9 cm. Width, lateral lobes: About 1.5 cm. Length, central lobe: About 1.9 cm. Width, central lobe: About 5 mm to 20 mm. Length, cirrhose tips: About 1.5 cm. Shape, lateral lobes: Obovate. Shape, central lobe: Broadly deltoid with an elongated apex. Apex, lateral lobes: Obtuse. Apex, central lobe: Acute with two upwardly and backwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 5 mm in length, about 6 mm in width and about 5 mm in height. Color: When opening, upper surface: Lateral lobes: Close to NN155D; towards the lower margins, close to 1A; at the base, axial stripes, close to 64A. Central lobe: Close to NN155D; midrib and towards the base, close to 151D and at the base, close to 150D with radial stripes, close to 183D; cirrhose tips, close to NN155D. Callosities: Close to NN155A; towards the apex, close to 10A; fine dots, close to 177B. When opening, lower surface: Lateral lobes: Close to NN155D; towards the lower margins, close to 1B. Central lobe: Close to NN155B; midrib, close to 150D; towards the base, close to 151D and at the base, close to 157B; cirrhose tips, close to NN155B. Fully opened, upper surface: Lateral lobes: Close to NN155D; towards the lower margins, close to 5A; at the base, axial stripes, close to 64A. Central lobe: Close to NN155D; midrib and towards the base, close to 151C and 151D and at the base, close to 155C with radial stripes, close to 184B; narrow marginal edges, close to 153C; cirrhose tips, close to NN155D. Callosities: Close to NN155A; towards the apex, close to 1B; fine dots, close to 177B. Fully opened, lower surface: Lateral lobes: Close to NN155D; towards the lower margins, close to 5A. Central lobe: Close to NN155D; midrib, close to 150D; towards the base, close to 151C and at the base, close to 157D; narrow marginal edges, close to 153C; cirrhose tips, close to NN155D.

*Sepals*.—Quantity and arrangement: Three, one upper dorsal sepal and two lower lateral sepals. Length, dorsal sepal: About 3.9 cm. Width, dorsal sepal: About 2.6 cm. Length, lateral sepals: About 3.8 cm. Width, lateral sepals: About 2.4 cm. Shape, dorsal sepal: Ovate to roughly oblong. Shape, lateral sepals: Ovate. Apex, dorsal sepal: Obtuse. Apex, lateral sepals: Bluntly acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to 157D. When opening, lower surface: Close to a blend of 145C and 150C; towards the margins and apex, close to 150D. Fully opened, upper surface: Close to NN155D. Fully opened, lower surface: Close to 155C; towards the margins and apex, close to NN155C. Color, lateral sepals: When opening, upper surface: Close to 157D; towards the base, close to 145B to 145C. When opening, lower surface: Close to 145C and 145D; towards the base, close to 145B. Fully opened, upper surface: Close to NN155B; at the base, close to 145D. Fully opened, lower surface: Close to 155C; towards the margins and apex, close to 145C.

*Peduncles*.—Length: About 42.4 cm. Diameter: About 5 mm. Strength: Strong. Aspect: Upright to outwardly arching. Texture and luster: Smooth, glabrous; matte. Color: Close to a blend of NN137B and 146A; heavily dotted with fine dots, close to 144B.

*Pedicels*.—Length: About 2.9 cm. Diameter: About 3 mm. Strength: Moderately strong. Aspect: About 60° from peduncle axis. Texture and luster: Smooth, glabrous; matte. Color: Close to 144B; proximally, close to 144A and distally, close to 145D.

*Reproductive organs*.—Androecium: Column length: About 8 mm. Column width: About 5.5 mm. Column color: Close to NN155D. Pollinia quantity: Two. Pollinia diameter (per two pollinia): About 3 mm. Pollinia color: Close to 23A. Gynoecium: Stigma length: About 3 mm. Stigma width: About 4 mm. Stigma shape: Reniform. Stigma color: Close to 157D. Ovary length: About 7 mm. Ovary diameter: About 1 mm. Ovary color: Close to 149A and 149B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA568949' as herein illustrated and described.

* * * * *